(12) United States Patent
Sanz et al.

(10) Patent No.: US 7,931,742 B2
(45) Date of Patent: Apr. 26, 2011

(54) BIOCIDAL STRUCTURAL BARRIER (BSB)

(75) Inventors: Daniel Sanz, Ayguemorte les Graves (FR); Eric Cazeneuve, Pyla sur Mer (FR)

(73) Assignees: BASF SE, Ludwigshafen (DE); Sep Innovaterm, Bordeaux (FR)

( * ) Notice: Subject to any disclaimer, the term of this patent is extended or adjusted under 35 U.S.C. 154(b) by 0 days.

(21) Appl. No.: 12/092,019

(22) PCT Filed: Nov. 2, 2006

(86) PCT No.: PCT/EP2006/068030
§ 371 (c)(1),
(2), (4) Date: Apr. 29, 2008

(87) PCT Pub. No.: WO2007/051814
PCT Pub. Date: May 10, 2007

(65) Prior Publication Data
US 2008/0229970 A1    Sep. 25, 2008

(30) Foreign Application Priority Data

Nov. 2, 2005    (FR) ...................... 05 11115
Aug. 3, 2006    (FR) ...................... 06 07122

(51) Int. Cl.
*A01N 43/36*    (2006.01)
*A01N 33/00*    (2006.01)
*C04B 24/12*    (2006.01)
*C04B 103/67*   (2006.01)
*C04B 111/20*   (2006.01)

(52) U.S. Cl. ............. 106/18.32; 106/15.05; 106/18.35; 106/727; 106/808; 106/823; 514/427; 514/428

(58) Field of Classification Search ............... 106/15.05, 106/18.32, 18.33, 18.34, 18.35, 18.36, 724, 106/725, 727, 728, 802, 808, 809, 810; 514/427, 514/428
See application file for complete search history.

(56) References Cited

U.S. PATENT DOCUMENTS

| | | | |
|---|---|---|---|
| 5,977,148 A * | 11/1999 | Matsuda et al. | 514/357 |
| 2004/0040245 A1 | 3/2004 | Sinclair, Sr. et al. | |
| 2005/0126430 A1 | 6/2005 | Lightner, Jr. et al. | |
| 2007/0039235 A1 * | 2/2007 | Yoshida et al. | 43/124 |

FOREIGN PATENT DOCUMENTS

| | | |
|---|---|---|
| FR | 2 848 551 | 6/2004 |
| JP | 63-55239 A * | 3/1988 |
| JP | 03-55336 A * | 3/1991 |
| JP | 03055336 | 3/1991 |
| JP | 07-291699 A * | 11/1996 |
| JP | 010017351 | 1/1998 |
| JP | 2000 103703 | 4/2000 |
| JP | 2005 154364 | 6/2005 |
| KR | 970008740 | 5/1997 |
| WO | WO 02/15684 | 2/2002 |
| WO | WO 02/082906 | 10/2002 |
| WO | WO2005/032253 A1 * | 4/2005 |
| WO | WO2007/052705 A1 * | 5/2007 |

OTHER PUBLICATIONS

Worthing, C.R. et al., "The Pesticide Manual", 10th edition, Pesticide Manual World Compendium, Farnham, BCPC, GB, vol. ED. 10, 1995, p. 1335-1341, XP 002031460, Search Report.

* cited by examiner

*Primary Examiner* — Anthony J Green
(74) *Attorney, Agent, or Firm* — Brinks Hofer Gilson & Lione

(57) ABSTRACT

A biocidal structural barrier of a raw concrete or a structure made of concrete is provided containing a specific insecticidal biocide product and/or a repellent that has been incorporated throughout the mass. The invention is particularly suitable for the building and construction sector and more particularly for concrete structures located close to the soil or in the soil (slab, foundations, buried walls, prefabricated concrete blocks, etc.). The preferred insecticide for protection against termites is chlorfenapyr.

18 Claims, No Drawings

BIOCIDAL STRUCTURAL BARRIER (BSB)

This application is a National Stage application of International Application No. PCT/EP2006/068030 filed Nov. 2, 2006, the entire contents of which are hereby incorporated herein by reference.

The invention relates to a concrete composition comprising an insecticidal biocide product and/or repellent product, a process for its manufacture and its use in the construction field to make structures which are nonnegotiable to arthropods, such as insects, like termites and ants, that invade habitations and constructions of all kinds, thus providing a physicochemical biocidal barrier.

The invention is intended to be used in the field of the construction of private dwellings (for example individual houses), communal dwellings, nonresidential buildings (offices, commercial premises, etc.) and also any construction requiring the use of concrete. More precisely, the invention is intended to be used for the construction of concrete foundations, concrete slabs located on the ground floor of the construction, and also concrete buried walls (for example the walls of cellars or garages or other premises located below ground level).

The present invention is also intended to be used in the manufacture of concrete structures such as prefabricated concrete blocks, and other concrete structures used in the building industry.

The presence of subterranean termites belonging to the genus *Reticulitermes* in Europe and in metropolitan France in particular and to the genera *Coptotermes, Heterotermes* and *Nasutitermes* in tropical areas like the French overseas departments represents a threat to constructions, in particular when they contain cellulosic elements.

To protect purchasers and owners from the nuisance caused by these insects when they attack buildings, the French Legislature has passed a law (Law No. 99-471) which provides two decrees of application. The first decree was published in July 2000. It sets the measures that must be taken by prefects and mayors to limit the propagation of insects and gives mayors policing powers in respect of preventing and combating them. The second decree, in draft at the time of writing this document, relates to Article 7 of Law No. 99-471. It will modify the CCH (Construction and Building Code) and will stipulate a number of measures that house builders and professionals fitting out premises of all types must take in order to protect the building from attack by insects having xylophagous larvae and termites.

Among the measures that are provided to be implemented, the order relating to the 2nd decree lists devices intended to be installed between the soil and a new construction:
  physicochemical barriers;
  physical barriers;
  constructional devices.

Subterranean termites belong to the order Isoptera. They are social insects living in colonies of several thousands to several millions of individuals, in which they are organized in castes: workers, soldiers, primary reproductives and neotenous adults. In most cases, the colony is located in the soil (this is the reason why they are called subterranean termites). The function of the soldiers is to protect the colony. They do not feed directly but are fed by the workers. The primary reproductives and the neotenous adults (secondary reproductives) have the function of reproducing and of ensuring development of the colony. They do not feed but, like the soldiers, are fed by the workers. The workers represent the most numerous caste (about 80% to 90%). These are responsible for foraging for food (cellulose, which is found in wood, cardboard, paper and other cellulosic materials) that they regurgitate to their congenera (food exchange by trophallaxy).

The prospecting behavior of the workers is neverending. Thus, they drill into the soil in all directions in search for sources of food. When a source of food is identified, the number of workers visiting this source increases with time, this being manifested by an increase in deposition of track pheromones deposited by the workers during their passage. The presence of track pheromones increases the frequenting of the food source. However, it should be noted that some of the workers continue to prospect for other food sources, thus ensuring the perpetuity of the colony over time.

When a colony is present near a construction, the termite workers may invest the building randomly with their prospecting. As they move around in the soil, the preferential sites for entry into the building are located in the regions lying between the soil and the base of the construction.

In old constructions, without a concrete slab, the termites can infest the building via the entire base, in particular when this rests on the soil via a floor.

In recent constructions, the presence of a concrete slab forms an obstacle to penetration, except when it cracks, leaving space for passage of the insects (average size: 5 mm in length and 2 mm in diameter). In addition, the reservations needed for passage of the drains and various ducts (for water, gas, electricity, etc.) are preferential sites and therefore constitute weak points.

Thus, within the scope of the 2nd decree aimed at protecting new constructions and modifications of all kinds, it is recommended to use devices for preventing termites present in the soil from penetrating the construction using either the sinuosities of the concrete slab, or the spaces around the reservations.

In order to provide physicochemical barriers against the penetration of harmful arthropods, like termites and ants, into a building it is known to impregnate the surface of walls and the foundation of a building with an insecticide (see e.g. G. Buczkkowski et al., J. Econ. Entomol. 98 (2005) 485-492), B. Kard, Pest Control 61 (1993) 50-54). However, the disadvantages of such methods include the increased risk of the pesticide leaching into the ground, which reduces efficacy and is undesirable from an ecological point of view. Further, if cracks appear in such a structure the barrier tends to become ineffective quite rapidly.

It has been suggested (see summary in: ACI Journal, Proceedings V.56 (1960) 904) to grind certain persistent organochlorine insecticides, like dieldrine, into cement or add them as admixtures. However, while the persistency of these chemicals may be favorable to ensure a long lasting performance even under the condition of a concrete mixture, it is highly undesirable from an ecological standpoint. For this reason, and the high toxicity of those compounds they have been almost completely banned in most countries.

In general, much experience and careful control of concrete properties is required when additives are used in concrete because their effects may depend on many parameters, such as concrete composition, type of cement, and temperature. The simultaneous use of more than one additive may lead to further problems because of interferences, and to undesired properties.

It has now been found that certain classes of insecticidal biocides are particularly useful for incorporation into concrete mixtures to provide an effective, enduring insecticidal action while avoiding environmental concerns.

Therefore, in one aspect of the invention there is provided a concrete composition, comprising—incorporated into the mass of the concrete—an additive of the insecticidal biocide and/or repellent type, which is selected from
(A1) organo(thio)phosphates, (A2) carbamates, (A3) pyrethroids, (A4) nicotinic receptor agonist/antagonist compounds, (A5) GABA antagonists of the fiprol type, (A6) macrocyclic lactone insecticides, (A7) METI I compounds, (A8) METI II and III compounds, (A9) uncoupler compounds, (A10) oxidative phosphorylation inhibitor compounds, (A11) moulting disruptor compounds, (A12) mixed function oxidase inhibitor compounds, (A13) sodium channel blocker compounds, (A14) malononitrile compounds, (A15) repellents and (A16) the compounds amitraz, benclothiaz, bifenazate, cartap, flonicamid, pyridalyl, pymetrozine, sulfur, thiocyclam, flubendiamide, cyenopyrafen, flupyrazofos, cyflumetofen, amidoflumet, the aminoquinazolinone compound of formula $\Gamma^4$

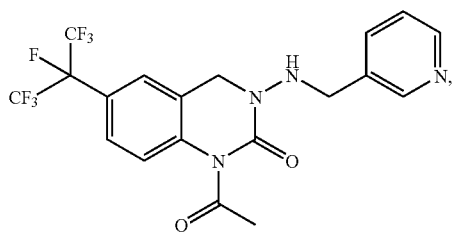

N—R'-2,2-dihalo-1-R"cyclo-propanecarboxamide-2-(2,6-dichloro-α,α,α-tri-fluoro-p-tolyl)-hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, anthranilamide compounds of formula $\Gamma^5$

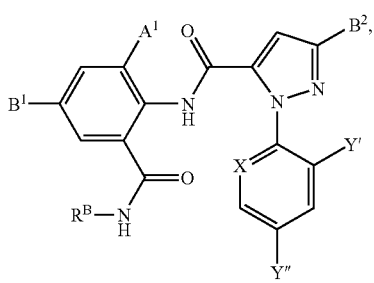

wherein A1 is CH3, Cl, Br, I, X is C—H, C—Cl, C—F or N, Y' is F, Cl, or Br, Y" is H, F, Cl, CF$_3$, B1 is hydrogen, Cl, Br, I, CN, B$_2$ is Cl, Br, CF3, OCH$_2$CF$_3$, OCF$_2$H, or OCF$_2$CHFOCF$_3$ and R$_B$ is hydrogen, CH$_3$ or CH(CH$_3$)$_2$.

Concrete slabs or walls made from the composition according to the invention provide excellent long lasting protection against harmful arthropods such as termites, and avoid the leaching of biocide into the ground or interior of the building. Since the biocide is added in the manufacture of the concrete composition extra steps to provide biocidal barriers are avoided, thus making the process also economically attractive.

In a further aspect of the invention there is provided a method of preparing the composition of the invention, in which the additive is incorporated directly into the composition or via a constituent of the composition.

In yet a further aspect of the invention, there is provided the use of the composition of the invention in the construction field.

In yet a further aspect of the invention there is provided a method for protecting a building from harmful arthropods, comprising the step of incorporating the composition of the invention into the groundworks and/or one or more walls of the building.

The term "biocide" as used in the following includes a product with an insecticidal and/or repellent activity.

The term "composition comprising an additive" as used herein means that the biocide is essentially homogenously incorporated into the mass of the concrete, as opposed e.g. to an impregnation of a porous outer layer of concrete on a wall, or the injection of an insecticide into a hole or crack in a concrete structure.

The term "insecticide" and "insecticidal" includes a killing or repelling action against any kind of harmful arthropods, e.g. also against arachnids.

The insecticidal biocide product or the repellant are chosen preferably such that they offer good resistance to degradation in alkaline medium or are formulated in such a way that the combination consisting of the formulation (insecticide+matrix, or repellant+matrix, or insecticide+repellant+matrix) exhibits good resistance to degradation in alkaline medium.

The biocide product may be composed of one or more substances that act on the nervous system of harmful arthropods such as harmful insects, on the cell energy generation process, or any other biological target, causing the death of the arthropods.

The repellant may be an insecticide or a product such that it diverts the arthropods, thus preventing penetration of the concrete by the arthropods, in particular at the cracks or defects that may be produced over time.

The insecticidal biocide product or the repellant preferably complies with the requirements of biocide Directive 98/8 CE of the European Union.

Examples of the biocide product include:

A.1. Organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

A.2. Carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

A.3. Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, empenthrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

A.4. Nicotinic receptor agonists/antagonists compounds: clothianidin, dinotefuran, imidacloprid, thiamethoxam, nitenpyram, acetamiprid, thiacloprid; the thiazol compound of formula ($\Gamma^1$)

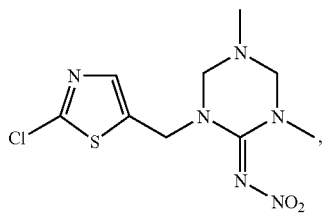

(I¹)

A.5. GABA antagonist compounds of the fiprol type: acetoprole, endosulfan, ethiprole, fipronil, vaniliprole, pyrafluprole, pyriprole, the phenylpyrazole compound of formula I²

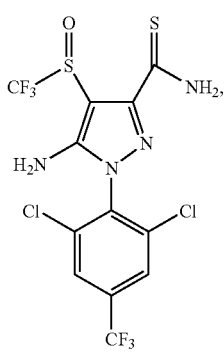

(I²)

A.6. Macrocyclic lactone insecticides: abamectin, emamectin, milbemectin, lepimectin, spinosad;
A.7. METI I compounds: fenazaquin, pyridaben, tebufenpyrad, tolfenpyrad, flufenerim;
A.8. METI II and III compounds: acequinocyl, fluacyprim, hydramethylnon;
A.9. Uncoupler compounds: chlorfenapyr;
A.10. Oxidative phosphorylation inhibitor compounds: cyhexatin, diafenthiuron, fenbutatin oxide, propargite;
A.11. Moulting disruptor compounds: cyromazine;
A.12. Mixed Function Oxidase inhibitor compounds: piperonyl butoxide;
A.13. Sodium channel blocker compounds: indoxacarb, metaflumizone,
A14. malonodiitrile compounds as described in JP 2002 284608, WO 02/89579, WO 02/90320, WO 02/90321, WO 04/06677, WO 04/20399, JP 2004 99597, WO 05/68423, WO 05/68432, or WO 05/63694, especially the malononitrile compounds $CF_3(CH_2)_2C(CN)_2CH_2(CF_2)_3CF_2H$, $CF_3(CH_2)_2C(CN)_2CH_2(CF_2)_5CF_2H$, $CF_3(CH_2)_2C(CN)_2(CH_2)_2C(CF_3)_2F$, $CF_3(CH_2)_2C(CN)_2(CH_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2CH_2C(CN)_2CH_2(CF_2)_3CF_2H$, and $CF_3CF_2CH_2C(CN)_2CH_2(CF_2)_3CF_2H$ and
A15. Repellents: N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella), IR3535 (ethyl butylacetylaminopropionate), and icaridin (1-piperidinecarboxylic acid 2-(2-hydroxyethyl)-1-methylpropylester)
A.16. Various: amitraz, benclothiaz, bifenazate, cartap, flonicamid, pyridalyl, pymetrozine, sulfur, thiocyclam, flubendiamide, cyenopyrafen, flupyrazofos, cyflumetofen, amidoflumet, the aminoquinazolinone compound of formula I⁻⁴

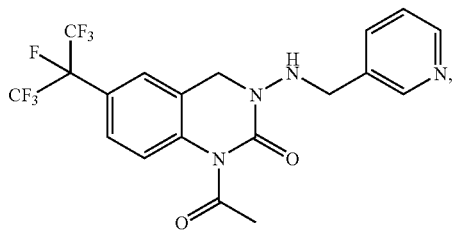

(I⁴)

N—R'-2,2-dihalo-1-R"cyclo-propanecarboxamide-2-(2,6-dichloro-α,α,α-tri-fluoro-p-tolyl)-hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, anthranilamide compounds of formula I⁻⁵

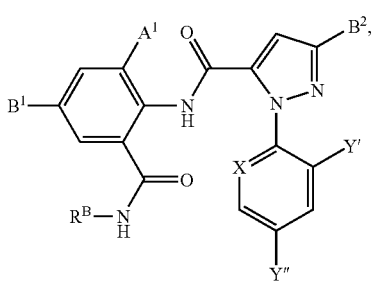

(I⁵)

wherein $A^1$ is $CH_3$, Cl, Br, i, X is C—H, C—Cl, C—F or N, Y' is F, Cl, or Br, Y" is H, F, Cl, $CF_3$, $B^1$ is hydrogen, Cl, Br, I, CN, $B^2$ is Cl, Br, $CF_3$, $OCH_2CF_3$, $OCF_2H$, or $OCF_2CHFOCF_3$ and $R^B$ is hydrogen, $CH_3$ or $CH(CH_3)_2$.

The commercially available compounds of the group A may be found in The Pesticide Manual, 13th Edition, British Crop Protection Council (2003) among other publications. Thioamides of formula I² and their preparation have been described in WO 98/28279. Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. Cyflumetofen and its preparation have been described in WO 04/080180. Anthranilamides of formula I⁵ and their preparation have been described in WO 01/70671; WO 02/48137; WO 03/24222, WO 03/15518, WO 04/67528; WO 04/33468; and WO 05/118552. The malononitrile compounds $CF_3(CH_2)_2C(CN)_2CH_2(CF_2)_3CF_2H$, $CF_3(CH_2)_2C(CN)_2CH_2(CF_2)_5CF_2H$, $CF_3(CH_2)_2C(CN)_2(CH_2)_2C(CF_2)_2F$, $CF_3(CH_2)_2C(CN)_2(CH_2)_2(CF_2)_3CF_3$, $CF_2H(CF_2)_3CH_2C(CN)_2CH_2(CF_2)_3CF_2H$, $CF_3(CH_2)_2C(CN)_2CH_2(CF_2)_3CF_3$, $CF_3(CF_2)_2CH_2C(CN)_2CH_2(CF_2)_3CF_2H$, and $CF_3CF_2CH_2C(CN)_2CH_2(CF_2)_3CF_2H$ have been described in WO 05/63694.

It is also possible to use mixtures of two or more biocides.

Preferred is the use of compounds from the classes (A3) pyrethroids, (A4) nicotinic receptor antagonists, (A5) GABA antagonists of the fiprol type, and (A9) uncoupler compounds.

Especially preferred are the biocides acephate, azamethiphos, azinphos-metyl, chlorpyrifos, chlorpyrifos-methyl, chlorfenvinphos, diazinon, dichlorvos, dicrotophos, dimethoate, disulfoton, ethion, fenitrothion, fenithion, isoxathion, malathion, methamidophos, methidathion, methylparathion, mevinphos, monocrotophos, oxydemeton-methyl, paraoxon, parathion, phenthoate, phosalone, phosmet, phosphamidon, phorate, phomixin, pirimiphos-methyl, profenofos, prothiofos, sulprophos, tetrachlorvinphos, terbufos, triazophos, trichlorfon;

allethrin, bifenthrin, cyflutrhin, cyhalothrin, cyphenothrin, cypermethrin, alpha-cypermethrin, beta-cypermethrin, zeta-cypermethrin, deltamethrin, empenthrin, esfenvalerate, etofenprox, fenpropathrin, fenvalerate, imiprothrin, lambda-cyhalothrin, permthrin, prallethrin, pyerthin I and II, resmethrin, silafoufen, taufluvalinate, tefluthrin, tetramethrin, tralomethrin, transfluthrin, profluthrin, dimefluthrin, a) chitin inhibitors: benzoylureas: chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxcarb; d) lipid biosynthesis inhibitors: spirodiclofen, spiromesifen, spirotetramat;

clothianidin, dinotefuran, imidacloprid, thiamethoxam, nitenpyram, acetamiprid, thiacloprid;

the thiazol compound of formula ($\Gamma^1$)

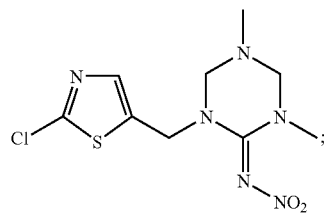

acetoprole, endosulfan, ethiprole, fipronil, vaniliprole, pyrafluprole, pyriprole, the phenylpyrazole compound of formula $\Gamma^2$

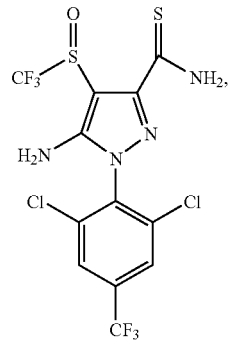

and chlorfenapyr.

More preferred biocides are α-cypermethrin, bifentrin, chlorfenapyyr, chlorpyrifos, deltamethrin, fipronil, hexaflumuron, imidacloprid, permethrin, and triflumuron.

Very particularly preferred are fipronil and chlorfenapyr, especially chlorfenapyr.

The dose rate of the biocide varies in a broad range depending on the type of insecticide, the type of concrete, the desired application etc.

In general, it is in the range of 0.001 to 10 g/kg of the concrete composition, preferably 0.01 to 2 g/kg of the concrete composition, in particular 0.05 to 0.5 g/kg of the concrete composition.

Usually the biocide is dissolved or dispersed in an aqueous medium before incorporation into the concrete mixture. Since many biocides are not well soluble in water it is advantageous to use formulated biocides to ensure a good dispersion. In principle, any customary formulation type, such as a suspension concentrate (SC), is suitable, as long as the biocide is well dispersed. However, it is preferable to avoid large amounts of solvents in order not to deteriorate the properties of the concrete mix.

The biocide product is effective against termites and other harmful arthropods that infest buildings (ants, spiders, etc.) in the sense that it prevents the termites and possibly the other arthropods from passing through the physicochemical barrier or that these organisms die after having passed through the barrier. The repellant is capable of preventing termites and other arthropods from passing through the physicochemical barrier without necessarily causing the death of the targeted organisms.

Some of the possible harmful arthropods include:

Examples of such organisms are:

subterranean termites (Isoptera), e.g. *Reticulitermes flavipes, Reticulitermes hesperus, Reticulitermes virginicus, Reticulitermes lucifugus, Reticulitermes santonensis, Reticulitermes banyulensis, Reticulitermes grassei,* and *Coptotermes formosanus, Heterotermes aureus* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp. *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile,*

The biocide product may be incorporated into the concrete in various ways: either directly during manufacture of the cement, directly during manufacture of the concrete, or in a material or element (gravel, cement, water, etc.) used for manufacturing the concrete, or in a material or element involved in the process of manufacturing the concrete.

In principle, any type of concrete can be used for the concrete mixture according to the invention, including in addition to normal concrete light weight concrete, heavy weight concrete, massive concrete, fiber-reinforced concrete, polymer concrete and mortar.

Apart from the biocide according to the invention, the concrete composition mainly comprises (a) cement, (b) aggregates, (c) water and (d) optionally further additives.

In principle, any kind of cement component (a) is suitable such as portland cement, including white portland cement, portland slag cement, portland pozzolano cement, portland fly-ash cement, pozzolanic cement and trass cement, blast furnace cement, cements with high sulfate resistance, cements with a low heat of hydration, low alkali cements, supersulfated cements, water repellent cements, oil well cements, regulated set cements, expanding cements, masonry cements, and high alumina cements.

The cement component generally constitutes about 25% of the volume of the concrete composition.

The aggregate component (b) acts as filler and may comprise any kind of aggregate, such as sand, including natural and artificial aggregates; light, normal or heavyweight aggregates; and mineral, metallic and organic materials. The particle size distribution of the aggregates is usually in the range of from 0.01 to 100 mm. Generally, the aggregates constitute up to 75% of the volume of the concrete.

Component (c) is water, which may contain the dispersed biocide, and which otherwise should be preferably contain as little as possible of impurities like organic compounds or salts.

In addition to the biocide of the invention, the concrete mix optionally comprises further customary additives. Such additives may include setting and hardening additives, like accelerators, or set retarding agents, workability additives, like plasticizers and superplasticizers, porosity additives, like foam-forming additives or air-removing additives, expansion-producing agents, corrosion inhibitors, fungicidal or microbicidal agents, damp-proofing and permeability-reducing additives, bonding agents and pigments, as well as fine grained materials, like unreactive rock material, reactive minerals, silica fume and metal oxide coloring agents, or polymers.

To prepare the concrete composition of the invention the biocide or a concentrated dispersion thereof is preferably mixed with the water, which is preferably added to the cement into which the aggregates are then incorporated.

To achieve a thoroughly mixed and homogenous fresh concrete, the materials are preferably charged into mixers which generally consist of revolving drums equipped with blades, stationary or revolving pans in which blades rotate on vertical shafts, or horizontal drums in which spiral blades operate on a rotating horizontal shaft. The necessary mixing time depends on the intensity of mixing, as well as on the batch size, and normally ranges from 30 to 120 s. Truck-mixed concrete may require up to 100 revolutions of the truck-mounted drum rotating at mixing speed.

The concrete composition of the invention is generally used in the construction field, preferably in the manufacturing of prefabricated concrete structures and the building industry.

The invention thus provides a physicochemical barrier, the physical part of which is formed by concrete and the chemical part is formed by a biocide product and/or that is incorporated throughout the mass of the concrete.

The composition is advantageously used in the construction of buildings, in particular for parts of the building which are in contact with the ground and, therefore, particularly susceptible to attack by termites and other harmful arthropods. Preferably, the concrete composition of the invention is used in foundations, groundworks or floors of buildings or in walls, preferably wall that are in contact with the ground, e.g. in concrete slabs or flagstones used in the construction of such walls and/or foundations.

More precisely, the composition is intended to be used for the construction of concrete foundations, concrete slabs located on the ground floor of the construction, and also concrete buried walls (for example the walls of cellars or garages other premises located below ground level).

The present composition is also intended to be used in the manufacture of concrete structures such as prefabricated concrete blocks, and other concrete structures used in the building industry.

Accordingly, the invention provides a method for protecting a building from harmful arthropods, by incorporating a composition of the invention into the groundwork or one or more walls of the building.

In a further aspect a building is provided, which comprises a composition of the invention in its groundwork and/or one or more of its walls.

The building can be any kind of building which is susceptible to attack by harmful arthropods, like termites, e.g. a residential building, a communal dwelling, a nonresidential building, like an office, a warehouse, an industrial building or a stable.

It goes without saying that when reference to the inventive composition is made in this application it refers to the raw composition in the context of manufacturing and to the cured composition in the context of buildings.

The invention is further illustrated by the following examples without limiting it thereby.

EXAMPLE

Determination of the Anti-Termite Effectiveness of Chlorfenapyr for Wall Treatment Test Set-Up A block of concrete, 10 cm high, with passages for the termites, is poured, incorporating the treatment product in the mixing water.

After drying and an infiltration test, the test set-up and performance follow the standard NF X41-541. The barrier effect of the specimen is verified by evaluation of the mortality and penetration of the termites in the clean compartment containing blocks of wood. An evaluation of the blocks of wood following the scoring of EN NF 117 is performed at the end of the test.

| | |
|---|---|
| Insecticide | chlorfenapyr (commercial formulation Mythic ®) 21.5 m/m |
| Characteristics of the concrete: | High yield concrete ready to be moistened, with a base of cement, sand and gravel, for construction work (foundations, finishing, slabs . . . ) |
| Dilution used in the mixing water: | 0.25-0.50-1.50-3% m/m |
| Density of the product: | 1106-1126 kg/m3 |
| Proportion water/cement | 3.5 litres of water for 30 kg of BPE |

-continued

| | |
|---|---|
| ready to use (BPE): Infiltration test: | According to standard NF X 41-542 (September 1995) |

Table of Results

| Concentration studied % (m/m) | No. | Retention of the product in the concrete ppm | Retention of the chlorfenapyr in the concrete ppm | Retention of the chlorfenaypr in the concrete g/m³ | Rate of survival % |
|---|---|---|---|---|---|
| Controls 0 | T1 | 0 | 0 | 0 | 72 |
| | T2 | | | | 87 |
| | T3 | | | | 75 |
| | T4 | | | | 81 |
| A 0.05 | A1 | 261 | 56 | 132 | 0 |
| | A2 | | | | 0 |
| | A3 | | | | 0 |
| | A4 | | | | 0 |
| B 0.1 | B1 | 521 | 112 | 265 | 0 |
| | B2 | | | | 0 |
| | B3 | | | | 0 |
| | B4 | | | | 0 |
| C 0.3 | C1 | 1567 | 337 | 795 | 0 |
| | C2 | | | | 0 |
| | C3 | | | | 0 |
| | C4 | | | | 0 |
| D 0.6 | D1 | 3132 | 673 | 1588 | 0 |
| | D2 | | | | 0 |
| | D3 | | | | 0 |
| | D4 | | | | 0 |

The tests show that concrete treated with chlorfenapyr effectively prevents termites from attacking a building.

The invention claimed is:

1. A method for protecting a building comprising concrete from harmful arthropods, said method comprising incorporating chlorfenapyr essentially homogenously into the concrete in one or more of (a) building foundation, (b) building groundworks, (c) one or more walls of the building.

2. The method of claim 1, wherein chlorfenapyr is present in an amount of from 0.001 to 10 g/kg of the concrete.

3. The method of claim 1, wherein chlorfenapyr is present in an amount of from 0.01 to 2 g/kg of the concrete.

4. The method of claim 3, wherein the harmful arthropods is a termite (the order of Isoptera).

5. The method of claim 4, wherein said termite is selected from the group consisting of *Reticulitermes flavipes, Reticulitermes hesperus, Reticulitermes virginicus, Reticulitermes lucifugus, Reticulitermes santonensis, Reticulitermes banyulensis, Reticulitermes grassei*, and *Coptotermes formosanus*.

6. The method of claim 1, wherein the harmful arthropods is a termite (the order of Isoptera).

7. The method of claim 6, wherein said termite is selected from the group consisting of *Reticulitermes flavipes, Reticulitermes hesperus, Reticulitermes virginicus, Reticulitermes lucifugus, Reticulitermes santonensis, Reticulitermes banyulensis, Reticulitermes grassei*, and *Coptotermes formosanus*.

8. A building comprising concrete in which chlorfenapyr is essentially homogenously incorporated into the concrete of (a) its foundation or (b) one or more of its walls.

9. The building of claim 8, wherein chlorfenapyr is present in an amount of from 0.001 to 10 g/kg of the concrete.

10. The building of claim 8, wherein chlorfenapyr is present in an amount of from 0.01 to 2 g/kg of the concrete.

11. A method for protecting a building comprising concrete or for protecting concrete by itself from harmful arthropods, said method comprising the step of incorporating chlorfenapyr directly during manufacture of the concrete.

12. The method of claim 11, wherein the harmful arthropods are termites.

13. A method for protecting a building comprising concrete or for protecting concrete by itself from harmful arthropods, said method comprising incorporating chlorfenapyr in a material or element used for manufacturing the concrete.

14. The method of claim 13, wherein the harmful arthropods are termites.

15. The method of claim 13, wherein the material or element is selected from the group consisting of gravel, cement and water.

16. A concrete in which chlorfenapyr is essentially homogenously incorporated.

17. The concrete of claim 16, wherein chlorfenapyr is present in an amount from 0.001 to 10 g/kg of the concrete.

18. The concrete of claim 16, wherein chlorfenapyr is present in an amount from 0.01 to 2 g/kg of the concrete.

* * * * *